United States Patent [19]

Sukhatme

[11] Patent Number: 5,206,152
[45] Date of Patent: Apr. 27, 1993

[54] CLONING AND EXPRESSION OF EARLY GROWTH REGULATORY PROTEIN GENES

[75] Inventor: Vikas P. Sukhatme, Chicago, Ill.

[73] Assignee: Arch Development Corporation, Chicago, Ill.

[21] Appl. No.: 249,584

[22] Filed: Sep. 26, 1988

Related U.S. Application Data

[63] Continuation-in-part of Ser. No. 179,587, Apr. 8, 1988, abandoned.

[51] Int. Cl.$^5$ .................. C07K 3/00; C07H 15/12
[52] U.S. Cl. .................................................. 435/69.1
[58] Field of Search .................. 435/69.1, 69.7, 91, 435/172.3, 252.33, 240.1, 235, 320, 258, 256; 536/27; 530/350; 935/18, 27, 31, 41, 48, 56, 58, 62, 70, 73, 81

[56] References Cited

U.S. PATENT DOCUMENTS 4,668,624 5/1987 Roberts et al. .................. 435/68

OTHER PUBLICATIONS

Sukhatme et al. Cell, vol. 53, pp. 37–43 (1988).
Lau et al. EMBO, J. vol. 4 pp. 3145–3151 (1985).
Maniahs et al. Molecular Cloning, A Laboratory Manual Cold Spring Harbor Laboratory, CSH, NY (1982).
Itakura et al., Science vol. 209 pp. 1401–1405 (1980).
Chavrier et al., EMBO, J., vol. 7, pp. 29–35 (1988).
Choudhury et al., Cell, vol. 48, pp. 771–778 (1987).
Sukhatme et al. Oncogene Research, vol. 1, pp. 343–355 (1987).
Manley et al., Proc. Nat'l Acad. Sci. USA, vol. 77, pp. 3855–3859 (1980).
Almendral, J. M., et al., Molecular and Cellular Biology, 8:2140–2148 (1988).
Chavrier, P., et al., EMBO, 7:29–35 (1988).
Pannuti, A., et al., Nucleic Acids Research, 16:4227–4237 (1988).
Rollins et al. (1988), Proc. Natl. Acad. Aci. USA, 85:3738–3742.
Oquendo et al. (1989), Jrnl. Biol. Chem., 264:4133–4137.

Primary Examiner—Joan Ellis
Attorney, Agent, or Firm—Arnold, White & Durkee

[57] ABSTRACT

Disclosed are DNA sequences encoding novel DNA binding proteins implicated in regulation of early stages of cell growth. Illustratively provided are human and mouse origin DNA sequences encoding early growth regulatory ("Egr") proteins which include "zinc finger" regions of the type involved in DNA binding. Also disclosed are immunological methods and materials for detection of Egr proteins and hybridization methods and materials for detection and quantification of Egr protein related nucleic acids.

12 Claims, 21 Drawing Sheets

FIG. 1.1

```
         10        20        30        40        50        60
GGGGAGCCGCCGGGCCGCCGGATTCGCCGGCCCAGCTTCCGCCGCCGGCCAAGATCGGCCCC 70        80        90       100       110       120
TGCCCCAGCCTCCGGCGCAGCCCTGCGTCCACCACGGGCCGGGCTACCGGCCAGCCTGGG 130       140       150       160       170       180
GGCCCCACCTACACTCCCCGCAGTGTGCCCCTGCACCCCGCATGTAACCCGGCCAACCCCC 190       200       210       220       230       240
GGCGAGTGTGCCCTCAGTAGCTTCGGCCCCGGGCTGCGCCCACCCAACATCAGTTCT 250       260       270       280       290       300
CCAGCTCGCTGGTCCGGGATGGCAGCGGCCAAGGCCGAGATGCAATGATGTCTCCGCTG
                              MetAlaAlaAlaLysAlaGluMetGlnLeuMetSerProLeu 310       320       330       340       350       360
CAGATCTCTGACCCGTTCGGCTCTCCTTCCTCACTCCACCATGGACAACTACCCCAAA
GlnIleSerAspProPheGlySerPheProHisSerProThrMetAspAsnTyrProLys 370       380       390       400       410       420
CTGGAGGAGATGATGCTGAGCAACGGGCTCCCCAGTTCCTCGGTGCTGCCGGAACC
LeuGluGluMetMetLeuLeuSerAsnGlyLeuProGlnPheLeuGlyAlaAlaGlyThr
```

FIG. 1.2

```
        430              440              450              460              470              480
CCAGAGGGCAGCGGCGGTAATAGCAGCAGCAGCACCAGCAGCGGGGCCGGTGGTGGGGGC
ProGluGlySerGlyGlyAsnSerSerGlySerSerThrSerSerGlyGlyGlyGlyGly 490              500              510              520              530              540
GGCAGCAACAGGCAGCAGCAGCGGCCCTTCAATCCTCAAGGGGAGCCGAGCGAACAACCCTAT
GlySerAsnSerGlySerSerAlaPheAsnProGlnGlyGluProSerGluGlnProTyr 550              560              570              580              590              600
GAGCACCTGACCACCAGAGTCCTTTCTGACATCGCTCTGAATAATGAGAAGGCGATGGTG
GluHisLeuThrThrArgValLeuSerAspIleAlaLeuAsnAsnGluLysAlaMetVal 610              620              630              640              650              660
GAGACGAGTTATCCCAGCCAAACGACTCGGTTGCCTCCCATCACCTATACTGGCCGCTTC
GluThrSerTyrProSerGlnThrThrArgLeuProProIleThrTyrThrGlyArgPhe 670              680              690              700              710              720
TCCCTGGAGCCCGCACCCAACAGTGGCAACACTTTGTGGCCTGAACCCCTTTTCAGCCTA
SerLeuGluProAlaProAsnSerGlyAsnThrLeuTrpProGluProLeuPheSerLeu 730              740              750              760              770              780
GTCAGTGGCCTCGTGAGCATGACCAATCCTCCGACCTCTTCATCCTCGGCCGCCTCTCCA
ValSerGlyLeuValSerMetThrAsnProProThrSerSerSerAlaProSerPro 790              800              810              820              830              840
GCTGCTTCATCGTCTTCCTGCCTCCCAGAGCCCGCCGCTGAGCTGTGCCGTGCCGTCC
AlaAlaSerSerSerSerAlaSerGlnSerProLeuSerProProLeuSerCysAlaValProSer
```

FIG. 1.3

```
           850            860            870            880            890            900
    AACGACAGCAGTCCCATCTACTCGGCTGCTGCCGCCCACCTTCCTACTCCCAAACACTGACATT
     AsnAspSerSerProIleTyrSerAlaAlaProThrPheProThrProAsnThrAspIle
           910            920            930            940            950            960
    TTTCCTGAGCCCCAAAGCCAGGCCTTCCTGCTCGGCAGGCACAGCCTTGCAGTACCCG
     PheProGluProGlnSerGlnAlaPheProGlySerAlaGlyThrAlaLeuGlnTyrPro
           970            980            990           1000           1010           1020
    CCTCCTGCCTACCCTGCCACCAAAGGTGGTTCCAGGTTCCCATGATCCCTGACTATCTG
     ProProAlaTyrProAlaThrLysGlyGlyPheGlnValProMetIleProAspTyrLeu
          1030           1040           1050           1060           1070           1080
    TTTCCACAACAACAGGGAGACCTGAGCCTGGGCACCCAGACCCCAGAAGCCCTTCCAGGT
     PheProGlnGlnGlnGlyAspLeuSerLeuGlyThrProAspGlnLysProPheGlnGly
          1090           1100           1110           1120           1130           1140
    CTGGAGAACCGTACCCAGAGCCTTCGCTCACTCCACTATCCACTATTAAAGCCTTCGCC
     LeuGluAsnArgThrGlnSerLeuArgSerLeuThrSerThrIleLysAlaPheAla
          1150           1160           1170           1180           1190           1200
    ACTCAGTCGGGCTCCCAGGACTTAAAGGCTCTTAATACCACCACCAATCCCAGCTCATC
     ThrGlnSerGlyAspLeuSerGlnAspLeuLysLeuAlaLeuAsnThrThrTyrGlnSerGlnLeuIle
          1210           1220           1230           1240           1250           1260
    AAACCCCAGCATGCGCAAGTACCCCAGAAGACACCCCCATGAACGC
     LysProSerArgMetArgLysTyrProAsnArgProSerLysThrProProHisGluArg
```

```
        1270      1280      1290      1300      1310      1320
CCATATGCTTGCCCTGTCGAGTCCTGCGATCGCCGCTTTCTGCTGATGAGCTTACC
ProTyrAlaCysProValGluSerCysAspArgArgPheSerArgAspGluLeuThr
  *         1330      1340    *  1350 FINGER I 1360      1370      1380
CGCCATATCCGCATCCACACAGGCCAGAAGCCCTTCCAGTGTCGAATCTGCGTAAC
ArgHisIleArgIleHisThrGlyGlnLysProPheGlnCysArgIleCysMetArgAsn
  *         1390      1400      1410    *    1420      1430      1440
TTCAGTCGTAGTGACCACCTTACCACCACATCCGCACCACAGGCGAGAAGCCTTTT
PheSerArgSerAspHisLeuThrThrHisIleArgThrHisThrGlyGluLysProPhe
  FINGER II   1450      1460    *    1470      1480      1490      1500
GCCTGTGACATTTGTGGGAGGAAGTTTGCCAGGAGTGATGAAACGCAAGAGGCATACCAAA
AlaCysAspIleCysGlyArgLysPheAlaArgSerAspGluArgLysArgHisThrLys
  *         1510      1520      1530      FINGER III 1540      1550      1560
ATCCATTTAAGACAGAAGGACAAGAAAGCAGACAAAAAGTGTGGGTCCTCCCCGGCTGCC
IleHisLeuArgGlnLysAspLysLysAlaAspLysLysSerValValAlaSerProAlaAla
          *  1570      1580      1590      1600      1610      1620
TCTTCACTCTCTTCTTACCCATCCTACCCCCAGTGGCTACCTCCTACCCATCCCCACC
SerSerLeuSerSerTyrProSerProValAlaThrSerTyrProSerProAlaThrThr
          1630      1640      1650      1660      1670      1680
TCATTCCCATCCCCTGTGCCCACTTCCTACTCCTCCTGGCTCCTCCACCTACCCATCT
SerPheProSerProValProThrSerTyrSerSerProGlySerSerThrTyrProSer
```

```
           1690       1700       1710       1720       1730       1740
CCTGCGCACAGTGGCTTCCCGTCCCGTCAGTGGCCACCACCTTTGCCTCCGTTCCACCT
ProAlaHisSerGlyPheProSerValAlaThrThrPheAlaSerValProPro 1750       1760       1770       1780       1790       1800
GCTTTCCCACCCAGGTCAGCAGCTTCCCGTCTGCGGGCGTCAGCAGCTCCTTCAGCACC
AlaPheProThrGlnValSerSerPheProSerAlaGlyValSerSerPheSerThr 1810       1820       1830       1840       1850       1860
TCAACTGGTCTCTTTCAGACATGACAGCGACCTTTCTCCCAGGACAATTGAAATTGCTAA
SerThrGlyLeuSerAspMetThrAlaThrPheSerProArgThrIleGluIleCys 1870       1880       1890       1900       1910       1920
AGGGAATAAAAGAAAGCAAAGGGAGAGGAGGAAAGACATAAAGCACAGGAGGAAGAG 1930       1940       1950       1960       1970       1980
ATGGCCGCAAGAGGGGCCACCCTCTTAGGTCAGATGGAAGATCTCAGAGCCAAGTCCTTCT 1990       2000       2010       2020       2030       2040
ACTCACGAGTAGAAGGACCGTTGGCCAACAGCCCTTTCACTTACCATCCCTGCCTCCCCC 2050       2060       2070       2080       2090       2100
GTCCTGTTCCCTTTGACTTCAGCTGCCTGAAACAGCCATGTCCAAGTTCTTCACCTCTAT
```

FIG. 1.6

```
         2110      2120      2130      2140      2150      2160
CCAAAGGACTTGATTTGCATGGTATTGGATAAATCATTTCAGTATCCTCTCCATCACATG 2170      2180      2190      2200      2210      2220
CCTGGCCCTTGCTCCCTTCAGGCGCTAGACCATCAAGTTGGCATAAAGAAAAAAATGGG 2230      2240      2250      2260      2270      2280
TTGGGCCCCTCAGAACCCTGCCCTGCATCTTTGTACAGCATCTGTGCCATGGATTTGTT 2290      2300      2310      2320      2330      2340
TTCCTTGGGTATTCTTGATGTGAAGATAAATTTGCATACTCTATTGTATTATTGGAGTT 2350      2360      2370      2380      2390      2400
AAATCCTCACTTTGGGGAGGGGGAGCAAAGCCAAGCAAACCAATGATGATCCTCTATT 2410      2420      2430      2440      2450      2460
TTGTGATGACTCTGCTGTGACATTAGGTTTGAAGCATTTTTTTTTCAAGCAGCAGTCCT 2470      2480      2490      2500      2510      2520
AGGTATTAACTGGAGCATGTGTCAGAGTGTGTTCCGTTAATTTTGTAAATACTGGCTCG
```

```
2530      2540      2550      2560      2570      2580
ACTGTAACTCTCACATGTGACAAAGTATGGTTTGTTTGGTTGGGTTTGTTTTTGAGAAT 2590      2600      2610      2620      2630      2640
TTTTTTGCCCGTCCCTTGGTTTCAAAAGTTTCACGTCTTGGTGCCTTTTGTGTGACACG 2650      2660      2670      2680      2690      2700
CCTTCCGATGGCTTGACATGCCGCAGATGTGAGGGACACGCTCACCTTAGCCTTAAGGGG 2710      2720      2730      2740      2750      2760
TAGGAGTGATGTGTTGGGGAGGCTTGAGAGCAAAACGAGGAAGAGAGGGCTGAGCTGAGC 2770      2780      2790      2800      2810      2820
TTTCGGTCTCCAGAATGTAAGAGAAGAAAATTTAACAAAAATCTGAACTCTCAAAAGTC
```

FIG. 1.7

```
       2830      2840      2850      2860      2870      2880
TATTTTCTAAACTGAGAAATGTAAATTATACATCTATTCAGGAGTTGGAGTGTTGTGGT 2890      2900      2910      2920      2930      2940
TACCTACTGAGTAGGCTGCAGTTTTTGTATGTTATGAACATGAAGTTCATTATTTTGTGG 2950      2960      2970      2980      2990      3000
TTTTATTTTACTTTGTACTTGTGTTTGCTTAAACAAAGTAACCTGTTTGGCTTATAAACA 3010      3020      3030      3040      3050      3060
CATTGAATGCGCTCTATTGCCCATGGGATATGTGGTGTATCCTTCAGAAAATTAAAA 3070      3080
GGAAAATAAAAAAAAAAAAAAAA
```

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| "Zinc finger" consensus sequence | T | G | E | K/R | P | Y/F | X | C | X | X | X | X | C | X | X | X | X | F | X | X | X | X | X | L | X | X | H | X | X | H |
| Murine Egr-1 | P | H | E | R | P | Y | A | C | P | V | E | S | C | D | R | R | F | S | R | S | D | E | L | T | R | H | I | R | I | H |
| | T | G | Q | K | P | F | Q | C | – | – | R | I | C | M | R | N | F | S | R | S | D | H | L | T | T | H | I | R | T | H |
| | T | G | E | K | P | F | A | C | – | – | D | I | C | G | R | K | F | A | R | S | D | E | R | K | R | H | T | K | I | H |
| Drosophila Kruppel | S | R | D | K | S | F | T | C | K | I | – | – | C | S | R | S | F | G | Y | K | H | V | L | Q | N | H | E | R | T | H |
| | T | G | E | K | P | F | E | C | P | E | – | – | C | D | K | R | F | T | R | D | H | H | L | K | T | H | M | R | L | H |
| | T | G | E | K | P | Y | H | C | S | H | – | – | C | D | R | Q | F | V | Q | V | A | N | L | R | R | H | L | R | V | H |
| | T | G | E | R | P | Y | T | C | E | I | – | – | C | D | G | K | F | S | D | S | N | Q | L | K | S | H | M | L | V | H |
| Xenopus TFIIIA (finger 2) | T | G | E | K | P | F | P | C | K | E | E | G | C | E | K | G | F | T | S | L | H | H | L | T | R | H | S | L | T | H |

```
         10          20         30         40         50         60
TTTTTTTTTTGGTGTGTGGTGTGTGTTTTTAAGTGTGGAGGGCAAAAGGAGATACCA 70         80         90        100        110        120
TCCCAGGCTCAGTCCAACCCCTCTCCAAAACNGTGTCTTTTCTGACACTCCAGGTAGCGA 130        140        150        160        170        180
GGGAGTTGGGTCTCCAGGTTGTGCGAGGAGCAAATGATGACCCGCCAAGGCCGTAGACAAA
                                 MetMetThrAlaLysAlaValAlaAspLys 190        200        210        220        230        240
ATCCCAGTAACTCTCAGTGTGGTTTTGTGCACCAGCTGTCTGACAACATCTACCCGGTGGAG
IleProValThrLeuSerGlyPheValHisGlnLeuSerAspAsnIleTyrProValGlu 250        260        270        280        290        300
GACCTCGCGCCACGTCGGTGACCATCTTTCCCAATGCCGAACTGGAGGCCCCTTTGAC
AspLeuAlaAlaThrSerValThrIlePheProAsnAlaGluLeuGlyGlyProPheAsp 310        320        330        340        350        360
CAGATGAACGGAGTGGCCGGAGATGCATGATCAACATTGACATGACTGGAGAGAAGAGG
GlnMetAsnGlyValAlaGlyAspMetIleAsnIleAspMetThrGlyGluLysArg
```

FIG. 3.1

```
        370             380             390             400             410             420
TCGTTGGATCTCCCATATCCCAGCAGCTTTGCTCCTCCGTCTCTGCACCTAGAAACCAGACC
SerLeuAspLeuProTyrProSerSerPheAlaProValSerAlaProArgAsnGlnThr 430             440             450             460             470             480
TTCACTTACATGGGCAAGTTCTCCATTGACCCACAGTACCCTGGTGCCAGCTGCTACCCA
PheThrTyrMetGlyLysPheSerIleAspProGlnTyrProGlyAlaSerCysTyrPro 490             500             510             520             530             540
GAAGGCATAATCAATATTGTGAGTGCAGGCATCTTGCAAGGGTCACTTCCCAGCTTCA
GluGlyIleIleAsnIleValSerAlaGlyIleLeuGlnGlyValThrSerProAlaSer 550             560             570             580             590             600
ACCACAGCCTCATCCAGGTCACCTCTGCCTCCCCAACCCACTGGCCACAGGACCCCTG
ThrThrAlaSerSerValThrSerAlaSerProAsnProLeuAlaThrGlyProLeu 610             620             630             640             650             660
GGTGTGTGCACCATGTCCCAGAGCCTGGACCACCTGTACTCTCCGCCACCG
GlyValCysThrMetSerGlnThrGlnProAspLeuAspHisLeuTyrSerProPro 670             680             690             700             710             720
CCTCCTCCTCCTTATTCTGGCTGTGCAGGAGACCTCTACCAGGACCCTTCTGGTTCCTG
ProProProTyrSerGlyCysAlaGlyAspLeuTyrGlnAspProSerAlaPheLeu
```

FIG. 3.2

```
        730        740        750        760        770        780
TCAGCAGCCACCACCCTCCACCTCTCCTCTGGCCTACCACCACCCTCCTTCCTATCCA
SerAlaAlaThrThrSerThrSerSerLeuAlaTyrProProProSerTyrPro 790        800        810        820        830        840
TCCCCCAAGCCAGCCAGGACCAGGTCTCTTCCCAATGATCCCAGACTATCCTGGATTC
SerProLysProAlaThrAspProGlyLeuPheProMetIleProAspTyrProGlyPhe 850        860        870        880        890        900
TTTCCATCTCAGTGCCAGAGAGACCTACAGTGTACAGCTGGCCCAGACCGTAAGCCCTTT
PheProSerGlnCysGlnArgAspLeuHisGlyThrAlaGlyProAspArgLysProPhe 910        920        930        940        950        960
CCCTGCCCACTGGACACCCTGGGGTGCCCCCCACTCCACTCCACTCTCTACAATCCGT
ProCysProLeuAspThrLeuArgValProProProLeuThrProLeuSerThrIleArg 970        980        990       1000       1010       1020
AACTTTACCCTGGGGGCCCCAGTGCTGGATGACCGGACCAGGGACCAGTGGAGGCAGC
AsnPheThrLeuGlyGlyProSerAlaGlyMetThrGlyProGlyAlaSerGlyGlySer 1030       1040       1050       1060       1070       1080
GAGGGACCCCGGCTGCCTGGTAGCAGCTCAGCAGCAGCAGCAGCCCGCCCCGCCGCC
GluGlyProArgLeuProGlySerSerSerAlaAlaAlaAlaAlaAlaAlaAlaAlaAla
```

FIG. 3.3

```
         1090       1100       1110       1120       1130       1140
TATAACCCACCACCACTGCCACTGCGGCCCATTCTGAGGCCTCGCAAGTACCCCAACAGA
TyrAsnProHisHisLeuProLeuArgProIleLeuArgProArgLysTyrProAsnArg 1150       1160       1170       1180       1190       1200
CCCAGCAAGACGCCCGGTGCACGAGAGGCCCTACCCGTGCCCAGCAGAAGGCTGCGACCGG
ProSerLysThrProValHisGluArgProTyrProCysProAlaGluGlyCysAspArg 1210       1220       1230       1240       1250       1260
CGGTTCTCCCGCTCTGACGAGCTGCATGCCAACATCCGAATCCACACTGGGCATAAGCCC
ArgPheSerArgSerAspGluLeuThrArgIleHisIleArgIleHisThrGlyHisLysPro 1270       1280       1290       1300       1310       1320
TTCCAGTGTCGGATCTGCATGCGCAACTTCAGCCGCAGTGACCACCTCACCACCCATATC
PheGlnCysArgIleCysMetArgAsnPheSerArgSerAspHisLeuThrThrHisIle 1330       1340       1350       1360       1370       1380
CGCACCCACACCGGTGAGAAGCCCTTCGCCTGTGACTACTGTGGCCGAAAGTTTGCCCGG
ArgThrHisThrGlyGluLysProPheAlaCysAspTyrCysGlyArgLysPheAlaArg 1390       1400       1410       1420       1430       1440
AGTGATGAGAGGAAGCGCCACCAAGATCCACCTGAGACAGAAAGAGCGGAAAAGCAGT
SerAspGluArgLysArgHisThrLysIleHisLeuArgGlnLysGluArgLysSerSer
```

FIG. 3.4

```
            1450      1460      1470      1480      1490      1500
         GCCCCCTCTGCATGGTGTGCCAGCCCCCTCTACAGCCCTCCTGCTCTGGGGGTGCAGGCC
          AlaProSerAlaSerValProAlaSerThrAlaSerCysSerGlyGlyValGlnAla 1510      1520      1530      1540      1550      1560
         TGGGGGTACCCTGTGCAGCAGTAACAGCAGTCTTGGCGGAGGGCCGCTCGCCCCTTG
          TrpGlyTyrProValGlnGlnEnd 1570      1580      1590      1600      1610      1620
         CTCCTCTCGGACCCGGAGACACCTTGAGATGAGACTCAGGCTGATACACCAGCTCCCAAAGG 1630      1640      1650      1660      1670      1680
         TCCCGGAGGCCCTTGTCCACTGGAGCTGCACAACAAACACTACCACCCCTTCCTGTCCC 1690      1700      1710      1720      1730      1740
         TCTCTCCCTTTGTTGGGCAAAGGGCTTGGTGGAGCTAGCACTGCCCCCTTTCCACCTAG 1750      1760      1770      1780      1790      1800
         AAGCAGGTTCTTCTCCTAAAACTTAGCCCCATTCTAGTCTCTCTTAGGTGAGTTGACTATCAA
```

FIG. 3.5

```
        1810      1820      1830      1840      1850      1860
CCCAAGGCAAAGGGGAGGCTCAGAAGGAGGTGGTGTGGGATCCCCTGGCCAAGAGGGCT 1870      1880      1890      1900      1910      1920
GAGGTCTGACCCTGCTTAAAGGGTTGTTTGACTAGGTTTTGCTACCCCACTTCCCCTTA 1930      1940      1950      1960      1970      1980
TTTTGACCCATCACAGGTTTTTTGACCCTGGATGTCAGAGTTGATCTAAGACGTTTCTAC 1990      2000      2010      2020      2030      2040
AATAGGTTGGGAGATGCTGATCCCCTTCAAGTGGGACAGCAAAAAGACAAGCAAAACTGA 2050      2060      2070      2080      2090      2100
TGTGCACTTTATGGCTTGGGACTGATTTGGGGGACATTGTACAGTGAGTGAAGTATAGCC 2110      2120      2130      2140      2150      2160
TTTATGCCACACTCTGTGGCCCTAAAATGGTGAATCAGAGCATATCTAGTTGTCTCAACC
```

FIG. 3.6

```
2170       2180       2190       2200       2210       2220
CTTGAAGCAATATGTATTATATACTCAGAGAACAGAAGTGCAATGTGATGGGAGGAACGT 2230       2240       2250       2260       2270       2280
AGCAATATCTGCTCCTTTCGAGTTGTGTTTGAGAAATGTAGGCTATTTTTTCAGTGTATAT 2290       2300       2310       2320       2330       2340
CCACTCAGATTTTGTGTATTTTTGATGTACCCACACTGTTCTCTAAATTCTGAATCTTTG 2350       2360       2370       2380       2390       2400
GGAAAAAATGTAAAGCATTTATGATCTCAGAGGTTAACTTATTTAAGGGGATGTACATA 2410       2420       2430       2440       2450       2460
TTCTCTGAAACTAGGATGCATGCAATTGTGTTGGAAGTGTCCCTTGGTCGCCCTTGTGTGAT 2470       2480       2490       2500       2510       2520
GTAGACAAATGTTACAAGGCTGCATGTAAAATGGGTTGCCTTATTATGGAGAAAAAATCA
```

FIG. 3.7

```
         2530      2540      2550      2560      2570      2580
      CTCCCTGAGTTTAGTATGGCTGTATATTTATGCCTATTAATATTCAAATTTTTTTAG 2590      2600      2610      2620      2630      2640
      AGTATATTTTGTATGCTTTGTTTGTGACTTAAAAGTGTTACCTTTGTAGTCAAATTC 2650      2660      2670      2680      2690      2700
      AGATAAGAATGTACATAATGTTACCGGAGCTGANNNTGTTTTGGTCATTAGCTCTTAATA 2710      2720      2730      2740      2750      2760
      GTTGTGAAAAAATAAATCTATTCTAACGCAAAACCACTAACTGAAGTTCAGATATAATGG 2770      2780      2790      2800      2810
      ATGGTTTGTGACTATAGTGTAAATAAATACTTTTCAACAAAAAAAAAAAAAAA
```

FIG. 3.8

```
-935 ACGGAGGGAA TAGCCTTTCG ATTCTGGGTG GTGCATTGGA AGCCCCAGGC TCTAAAACCC -876
-875 CCAACCTACT GACTGGTGGC CGAGTATGCA CCCGACTGCT AGCTAGGCAG TGTCCAAGAA -816
-815 ACCAGTAGCC AAATGTCTTG GCCTCAGTTT TCCGGGTGAC ACCTGGAAAG TGACCCTGCC -756
-755 ATTAGTAGAG GCTCAGGTCA GGGCCCCGCC TCTCCTGGGC GGCCTCTGCC CTAGCCCGCC -696
-695 CTGCCGCTCC TCCTCTCCGC AGGCTCGCTC CCACGGTCCC CGAGGTGGGC GGGTGAGCCC -636
-635 AGGATGACGG CTGTAGAACC CCGGCCTGAC TCGCCCTCGC CCCCGCGCCG GGCCTGGGCT -576
-575 TCCCTAGCCC AGCTCGCACC CGGGGGCCGT CGGAGCCGCC GCGCGCCCAG CTCTACGCGC -516
-515 CTGGCCCTCC CCACGCGGGC GTCCCCGACT CCCGCGCGCG CTCAGGCTCC CAGTTGGGAA -456
-455 CCAAGGAGGG GGAGGATGGG GGGGGGGGTG TGCGCCGACC CGGAAACGCC ATATAAGGAG -396
-395 CAGGAAGGAT CCCCCGCCGG AACAGACCTT ATTTGGGCAG CGCCTTATAT GGAGTGGCCC -336
```

FIG. 4.1

```
-335
AATATGGCCC TGCCGCTTCC GGCTCTGGGA GGAGGGGCGA GCGGGGGTTG GGGCGGGGGC  -276

-275
AAGCTGGGAA CTCCAGGCGC CTGGCCCGGG AGGCCACTGC CTGCTGTTCCA ATACTAGGCT  -216
                                     SmaI

-215
TTCCAGGAGC CTGAGCGCTC GCGATGCCGG AGCGGGTCGC AGGGTGGAGG TGCCCACCAC  -156

-155
TCTTGGATGG GAGGGCTTCA CGTCACTCCG GGTCCTCCCG GCCGGTCCTT CCATATTAGG  -96

-95
GCTTCCTGCT TCCCATATAT GGCCATGTAC GTCACGGGCG AGGCGGGCCC GTGCTGTTCC  -36

-35                              +1
AGACCCTTGA AATAGAGGCC GATTCGGGGA GTCGCGAGAG ATCCCAGCGC GCAGAACTTG  +25
              29-mer

+26
GGGAGCCGCC GCCGCGATTC GCCGCGCCG CCAGCTTCCG CCGCCGCAAG ATCGGCCCT   +85

+86
GCCCCAGCCT CCGCGGCAGC CCTGCGTCCA CCACGGGCCG CGGCTACCGC CAGCCTGGGG  +145

+146
GCCCACCTAC ACTCCCCGCA GTGTGCCCCT GCACCCCGCA TGTAACCCGG CCAACCCCCG  +205

+206
GCGAGTGTGC CCTCAGTAGC TTCGGCCCCG GGCTGCGCCC ACCACCCAAC ATCAGTTCTC  +265
                                     SmaI
```

FIG. 4.2

CLONING AND EXPRESSION OF EARLY GROWTH REGULATORY PROTEIN GENES

CROSS-REFERENCE TO RELATED APPLICATIONS

This is a continuation-in-part application of co-pending U.S. patent application Ser. No. 179,587, filed Apr. 8, 1988 now abandoned.

BACKGROUND OF THE INVENTION

The present invention relates generally to DNA binding regulatory proteins and more particularly to DNA sequences encoding early growth regulatory proteins possessing histidine-cysteine "zinc finger" DNA binding domains, to the polypeptide products of recombinant expression of these DNA sequences, to peptides and polypeptides whose sequences are based on amino acid sequences deduced from these DNA sequences, to antibodies specific for such proteins and peptides, and to procedures for detection and quantification of such proteins and nucleic acids related thereto.

Among the most significant aspects of mammalian cell physiology yet to be elucidated is the precise manner in which growth factors (e.g., hormones, neurotransmitters and various developmental and differentiation factors) operate to effect the regulation of cell growth. The interaction of certain growth factors with surface receptors of resting cells appears to rapidly induce a cascade of biochemical events thought to result in nuclear activation of specific growth related genes, followed by ordered expression of other genes. Analysis of sequential activation and expression of genes during the transition from a resting state ("G$_0$") to the initial growing state ("G$_1$") has been the subject of substantial research. See, generally, Lau et al., *Proc. Nat'l. Acad. Sci. (USA)*, 84, 1182–1186 (1987). Much of this research has involved analysis of the expression of known genes encoding suspected regulatory proteins (such as the proto-oncogenes, c-fos and c-myc) following mitogen stimulation. An alternative approach has involved attempts to identify genes activated by mitogenic stimuli through differential screening of cDNA libraries prepared from resting cells following exposure to serum and specific growth factors. See, e.g., Lau et al., *EMBO Journal*, 4, 3145–3151 (1985). See also, Cochran et. al., *Cell*, 33, 939–947 (1983), relating to the cloning of gene sequences apparently regulated by platelet derived growth factor.

Of interest to the background of the invention is the continuously expanding body of knowledge regarding structural components involved in the binding of regulatory proteins to DNA. Illustratively, the so-called receptor proteins are believed to bind to DNA by means of zinc ion stabilized secondary structural fingers premised on folding of continuous amino acid sequences showing high degrees of conservation of cysteines and histidines and hydrophobic residues. See, e.g., Gehring, *TIBS*, 12, 399–402 (1987). For example, a "zinc finger" domain or motif, present in Xenopus transcription factor IIIA (TF IIIA), as well as the Drosophila Kruppel gene product and various yeast proteins, involves "repeats" of about 30 amino acid residues wherein pairs of cysteine and histidine residues are coordinated around a central zinc ion and are thought to form finger-like structures which make contact with DNA. The histidine-cysteine (or "CC-HH") zinc finger motif, as opposed to a cysteine-cysteine ("CC-CC") motif of steroid receptors, is reducible to a consensus sequence represented as C-X$_{2-4}$-C-X$_3$-F-X$_5$-L-X$_2$-H-X$_3$-H wherein C represents cysteine, H represents histidine, F represents phenylalanine, L represents leucine and X represents any amino acid. [See, Klug et al. *TIBS*, 12, 464–469 (1987); Blumbeg et. al., *Nature*, 328, 443–445 (1987); and Schuh et al., *Cell*, 47, 1025–1032 (1986).]

Of particular interest to the background of the invention is the recent report of Chowdhury et al., *Cell*, 48, 771–778 (1987), relating to an asserted "family" of genes encoding proteins having histidine-cysteine finger structures. These genes, designated "mkr1" and "mkr2", appear to be the first such isolated from mammalian tissue and are not correlated to any early growth regulatory events.

There continues to exist a need in the art for information concerning the primary structural conformation of early growth regulatory proteins, especially DNA binding proteins, such as might be provided by knowledge of human and other mammalian DNA sequences encoding the same. Availability of such DNA sequences would make possible the application of recombinant methods to the large scale production of the proteins in procaryotic and eukaryotic host cells, as well as DNA-DNA and DNA-RNA hybridization procedures for the detection, quantification and/or isolation of nucleic acids associated with these and related proteins. Possession of such DNA-binding proteins and/or knowledge of the amino acid sequences of the same would allow, in turn, the development of monoclonal and polyclonal antibodies thereto (including antibodies to protein fragments or synthetic peptides modeled thereon) for use in immunological methods for the detection and quantification of early growth regulatory proteins in fluid and tissue samples as well as for tissue specific delivery of substances such as labels and therapeutic agents to cells expressing the proteins. In addition, DNA probes based on the DNA sequences for these mammalian early growth regulatory proteins may be of use in detecting gene markers used for the diagnosis of those clinical disorders which are linked to the marker genes.

BRIEF SUMMARY OF THE INVENTION

The present invention provides novel purified and isolated DNA sequences encoding mammalian early growth regulatory ("Egr") proteins which comprise one or more histidine-cysteine zinc finger amino acid sequences putatively providing DNA binding (and hence DNA replication or transcription regulatory) capacity. In presently preferred forms, novel DNA sequences of the invention comprise genomic and cDNA sequences encoding human and mouse early growth regulatory proteins. Alternate DNA forms, such as "manufactured" DNA, prepared by partial or total chemical synthesis from nucleotides, are also within the contemplation of the invention.

Operative association of Egr-encoding DNA sequences provided by the invention with homologous or heterologous species expression control DNA sequences, such as promoters, operators, regulators and the like, allows for in vivo and in vitro transcription to form messenger RNA which, in turn, is susceptible to translation to provide Egr proteins in large quantities. In one presently preferred DNA expression system practiced according to the invention, Egr-encoding DNA is operatively associated with a bacteriophage T3 or T7 RNA promoter DNA sequence allowing for in vitro transcription and translation in a cell free system. Incorporation of novel DNA sequences of the invention into procaryotic and eucaryotic host cells by standard transformation and transfection processes involving suitable viral and circular DNA plasmid vectors is also within the contemplation of the invention and is expected to provide useful proteins in quantities heretofore unavailable from natural sources. Illustratively, fragments of DNA encoding Egr protein of the invention have been incorporated in plasmid vectors resulting in expression by transformed E.coli hosts of fusion proteins sharing immunological characteristics of Egr protein. Use of mammalian host cells is expected to provide for such post-translational modifications (e.g., truncation, glycosylation, and tyrosine, serine or threonine phosphorylation) as may be needed to confer optimal biological activity on recombinant expression products of the invention.

Also provided by the present invention are novel, presumptively mitogen sensitive, DNA sequences involved in regulation of the transcription of Egr-encoding DNA, which sequences are expected to have utility in the efficient recombinant expression of Egr proteins as well as proteins encoded by other structural genes. In addition, the DNA sequences may be used as probes to detect the presence or absence of gene markers used for the diagnosis of clinical disorders linked to those gene markers.

Novel polypeptide products of the invention include polypeptides having the primary structural conformation (i.e., amino acid sequence) of Egr proteins or fragments thereof, as well as synthetic peptides, an analogs thereof, assembled to be partially or wholly duplicative of amino acid sequences extant in Egr proteins. Proteins, protein fragments, and synthetic peptides of the invention are expected to have therapeutic, diagnostic, and prognostic uses and also to provide the basis for preparation of monoclonal and polyclonal antibodies specifically immunoreactive with Egr proteins, as well as to provide the basis for the production of drugs for use as competitive inhibitors or potentiators of Egr. Preferred protein fragments and synthetic peptides of the invention include those duplicating regions of Egr proteins which are not involved in DNA binding functions (i.e., regions other than the zinc fingers). Most preferred are peptides which share at least one continuous or discontinuous antigenic epitope with naturally occurring Egr proteins.

Antibodies of the invention preferably bind with high immunospecificity to Egr proteins, fragments, and peptides, preferably recognizing epitopes which are not common to other proteins, especially other DNA binding proteins.

Also provided by the present invention are novel procedures for the detection and/or quantification of Egr proteins and nucleic acids (e.g., DNA and mRNA) specifically associated therewith. Illustratively, antibodies of the invention may be employed in known immunological procedures for quantitative detection of Egr proteins in fluid and tissue samples. Similarly, DNA sequences of the invention (particularly those having limited homology to other DNAs encoding DNA binding proteins) may be suitably labelled and employed for the quantitative detection of mRNA encoding the proteins. Information concerning levels of Egr mRNA may provide valuable insights into growth characteristics of cells.

Among the multiple aspects of the present invention, therefore, is the provision of (a) novel purified and isolated Egr-encoding DNA sequences set out in FIGS. 1.1–1.8, 3.1–3.8 and 4.1–4.2 as well as (b) Egr-encoding DNA sequences which hybridize thereto under hybridization conditions of the stringency equal to or greater than the conditions described herein and employed in the initial isolation of DNAs of the invention, and (c) synthetic or partially synthetic DNA sequences encoding the same, or allelic variant, or analog Egr polypeptides which employ, at least in part, degenerate codons. Correspondingly provided are viral or circular plasmid DNA vectors incorporating such DNA sequences and procaryotic and eucaryotic host cells transformed or transfected with such DNA sequences and vectors as well as novel methods for the recombinant production of Egr proteins through cultured growth of such hosts and isolation from the hosts or their culture media.

Preferred polypeptide products of the invention include those wholly or partially duplicating the deduced sequence of the amino acid residues set out in FIGS. 1.1–1.8 and 3.1–3.8 (i.e., mouse, "Egr-1" and human "EGR2"). Other preferred polypeptides include fusion proteins such as cro-$\beta$-galactosidase/Egr-1 and bovine growth hormone/Egr-1.

Presently preferred antibodies of the invention include those raised against synthetic peptides partially duplicating deduced Egr amino acid sequences of FIGS. 1A and 3 (e.g., the synthetic peptides H-L-R-Q-K-D-K-K-A-D-K-S-C, the first 12 amino acid residues of which duplicate mouse Egr-1 residues 416–427 with the last cysteine added for coupling to KLH; and C-G-R-K-F-A-R-S-D-E-R-K-R-H-T-K-I duplicating mouse Egr-1 residues 399–415). The antisera against the first peptide is designated VPS10 and comprises a preferred antibody of the invention.

As employed herein, the term "early growth regulatory protein" shall mean and include a mammalian DNA binding protein encoded by DNA whose transcription temporally corresponds to cellular events attending the $G_0/G_1$ growth phase transition. As employed herein, "histidine-cysteine zinc finger amino acid sequence" shall mean and include the following sequence of amino acids C-$X_{2-4}$-C-$X_3$-F-$X_5$-L-$X_2$-H-$X_3$-H wherein C represents cysteine, H represents histidine, F represents phenylalanine, L represents lysine, and X represents an amino acid.

Other aspects and advantages of the present invention will be apparent upon consideration of the following detailed description thereof which includes numerous illustrative examples of the practice of the invention reference being made to the drawing wherein:

FIGS. 1.1–1.8 provides a 3086 base nucleotide sequence for a mouse Egr-1 DNA clone as well as a deduced sequence of 533 amino acid residues for the protein; FIG. 1B provides a partial restriction map of Egr-1 DNA clones together with information concerning the position of the protein coding sequence and the locus of amino acids providing for histidine-cysteine zinc fingers;

FIG. 2 provides an amino acid sequence alignment of the DNA binding domain of mouse Egr-1 in comparison with a zinc finger consensus sequence, with the Drosophila Kruppel sequence and with the "finger 2" sequence of Xenopus TFIIIA protein;

FIGS. 3.1–3.8 provides a 2820 base nucleotide sequence for a human EGR2 cDNA clone as well as a deduced sequence of 456 amino acids for the protein;

FIGS. 4.1–4.2 provides a 1200 base nucleotide sequence of a mouse Egr-1 genomic clone, specifically illustrating the 5' non-transcribed regulatory region thereof comprising bases −935 through +1; and FIG. 5 provides a restriction map and organization of the mouse Egr-1 genomic clone mgEgr-1.1 and a comparison to mouse Egr-1 cDNA.

DETAILED DESCRIPTION

Figure 1B:
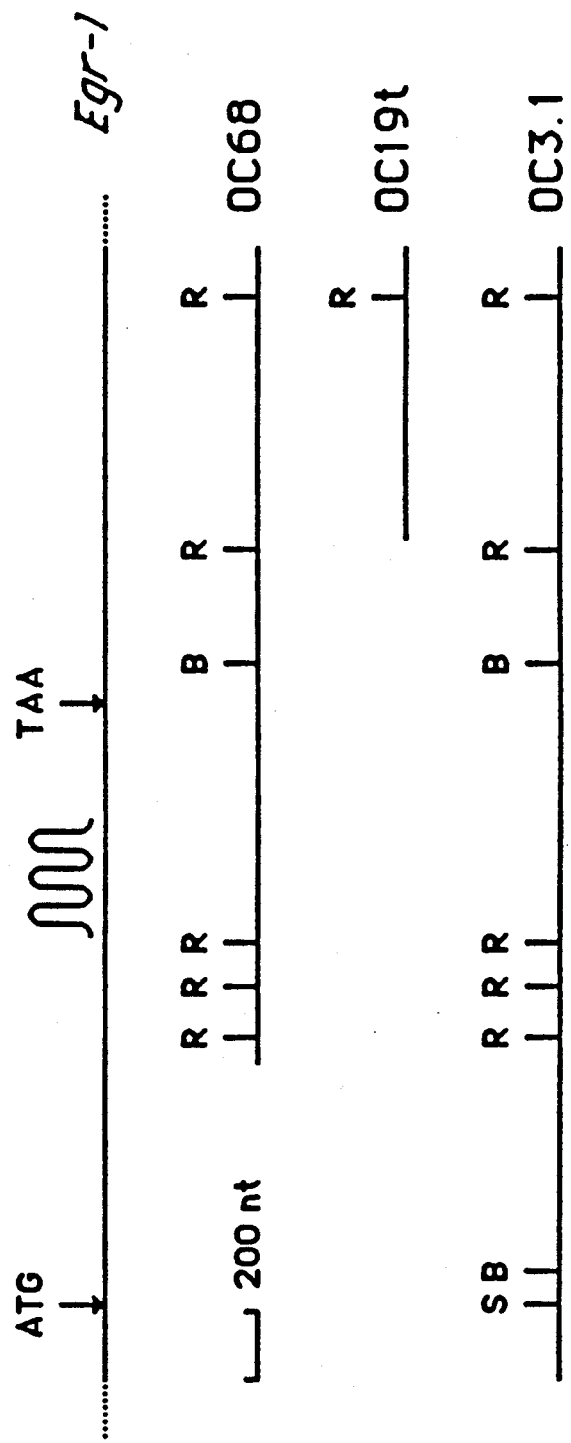

The following examples illustrate practice of the invention. Example 1 relates to the preparation and structural analysis of cDNA for mouse Egr-1. Example 2 relates to confirmation of the presence of an Egr DNA sequence on human chromosome 5. Example 3 relates to the in vitro transcription and translation of mouse Egr-1 cDNA. Example 4 relates to production of antibodies according to the invention. Example 5 relates to the isolation and characterization of genomic DNA which encodes mouse Egr-1. Example 6 relates to the isolation and characterization of cDNA encoding human EGR2. Example 7 relates to preparation, in an *E. coli* host, of a recombinant fusion protein including a portion of the deduced amino acid sequence of mouse Egr-1. Example 8 relates to use of DNA probes of the invention in the quantitative detection of EGR1 mRNA.

These examples are for illustrative purposes only and are not intended in any way to limit the scope of the invention.

EXAMPLE 1

Preparation and Structural Analysis of cDNA for Mouse Egr-1

Isolation of DNA encoding a mammalian early growth regulatory protein including one or more histidine-cysteine zinc finger amino acid sequences was performed substantially according to the procedures described in Sukhatme et al., *Oncogene Research*, 1, 343–355 (1987), the disclosures of which are specifically incorporated by reference herein.

Balb/c 3T3 cells (clone A31) from the American Type Culture Collection were grown to confluence in Dulbecco's Modified Eagle's medium (DME) supplemented with 10% fetal calf serum (FCS). The cells were rendered quiescent by reduction of the serum concentration to 0.75% for 48 hours. To induce the cells from quiescence into growth phase $G_1$, the medium was changed to 20% FCS with cycloheximide added to a final concentration of 10 µg/ml.

RNA was extracted from Balb/c 3T3 cells harvested three hours after induction of quiescent cells by 20% FCS and 10 µg/ml cycloheximide. A λgt10 cDNA library was constructed from this mRNA according to the procedures of Huynh et al., *DNA Cloning*, Vol. 1, 49–78 (Glover, D., ed., IRL Press, 1985). This library was screened differentially with single stranded cDNA prepared from quiescent cells and from cells exposed to serum and cycloheximide for 3 hours. These $^{32}$P-labeled cDNA probes were prepared from poly A+ RNA as described in St. John, et al., *Cell*, 16, 443–452 (1979), except that 100 µCi of $^{32}$P-dCTP (>3000 Ci/mmol), 0.02 mM cold dCTP and 2–5 µg of poly A+ RNA was used in each reaction. The mean size of the reverse transcribed probes, as assessed by alkaline agarose gel electrophoresis and subsequent autoradiography, was about 700 bases. Replica filter lifts (GeneScreenPlus, NEN-DuPont) were prepared essentially as described by Benton et al., *Science*, 196, 180–192 (1977), and approximately $3\times10^6$ cpm of $^{32}$P-cDNA were used per filter (90 mm diameter). Hybridizations were carried out at 65° C. in 1% SDS, 10% dextran sulfate, and 1 M NaCl for a period of 16 hours. The filters were washed twice for twenty minutes each time, first at room temperature in 2×SSC [Maniatis et al., *Molecular Cloning*, Cold Spring Harbor Laboratory (N.Y., 1982)], then at 65° C. in 2×SSC, 1% NaDodSO$_4$ and finally at 65° C. in 0.2×SSC. Autoradiograms were prepared by exposing the blots for 18 hours at −70° C. with an intensifying screen.

A total of 10,000 cDNA clones from the Balb/c 3T3 λgt10 library were differentially screened. Seventy-eight clones were found to hybridize preferentially to single-stranded cDNA from fibroblasts stimulated for 3 hours with 20% FCS and cycloheximide as compared to single-stranded cDNA from quiescent cells. Inserts from these clones were cross-hybridized to each other, resulting in the sorting of forty clones into 7 cDNA families one of which was identified as c-fos. Another cDNA clone, referred to as OC68, contained a 2.2 kb insert and was characterized further. This insert was subcloned into the Eco RI site of pUC13 and probes were generated for Northern blot analysis either from the insert or the corresponding pUC plasmid. FIG. 1B illustrates a partial restriction digest map of the OC68 clone ("R" representing restriction sites for RsaI) along with that of a shorter clone, OC19t. Two RsaI digestion fragments, derived from the 5' end of clone OC68 and each comprising approximately 130 base pairs, were labeled and employed to re-screen the above-described λgt10 cDNA library, resulting in the recovery of a 3.1 kb clone, designated OC3.1, shown in FIG. 1B. This clone was sequenced according to the method of Sanger et al., *Proc. Nat'l. Acad. Sci. (USA)*, 74, 5463 (1977). The 3086 base pair sequence obtained is set forth in FIGS. 1.1–1.8 along with the deduced sequence of 533 amino acid residues for the protein encoded, designated mouse "Egr-1".

The deduced amino acid sequence shows a single long open reading frame with a stop codon (TAA) at position 1858. The most 5', in-frame, ATG, at position 259, is flanked by sequences that fulfill the Kozak criterion ($G^4$NN(ATG)G) [Kozak, *Nuc. Acids Res.*, 15, 8125–8131 (1987)]. The sequence region upstream of this ATG is highly GC-rich and results in an absence of in-frame stop codons. The 3' untranslated region (UT) contains two "AT" rich regions (nucleotides 2550–2630 and 2930–2970). Similar sequences are found in the 3' UT regions of several lymphokine and proto-oncogene mRNAs, including granulocyte macrophage colony stimulating factor (GM-CSF), interleukin 1, interleukin 2, interleukin 3 (IL-3), α, β, and γ interferons, and c-fos, c-myc, and c-myb [Shaw et al., *Cell*, 46, 659–667 (1986)]. These sequences may mediate selective mRNA degradation. The presence in the mouse Egr-1 transcript of such regions is consistent with its short message half-life. Potential polyadenylation signals (AATAAA) re located at nucleotide positions 1865 and 3066, as well as at position 3053 (AATTAA) [Wickens et al., *Science*, 226, 1045–1051 (1984)].

The deduced amino acid sequence predicts a polypeptide of 533 amino acids with a molecular weight of 56,596. Based on structural considerations, namely a central region containing zinc fingers (described below), the Egr-1 protein can be divided into three domains. The N-terminal portion (amino acid residues 2 to 331) is rich in proline (14.2%) and serine (16%) residues with 7.9% alanines and 7.9% threonines. The C-terminal region (residues 417 to 533) also contains a very high proportion of prolines and serines (15.4 and 26.5%, respectively) and 10.3% alanines and 11.1% threonines. The large number of proline residues leads to a secondary structure that probably lacks α-helices. The central portion of the Egr-1 protein consists of three tandem repeat units of 28-30 amino acids, with the first unit starting at position 332. Each unit conforms almost exactly to the consensus sequence $TGX_3F^YXCX_2$-$4CX_3FX_5LX_2HX_3H$ (see FIG. 2), diagnostic of DNA binding zinc fingers [Berg, Science, 232, 485-486 (1986); Brown et al., Nature, 324, 215 (1986); and Brown et al., FEBS Letters, 186, 271-274 (1985)]. Furthermore, the Egr-1 fingers are connected by "H-C links" ($TGE_K^R$-$P_Y^FX$) [Schuh et al., Cell, 47, 1025-1032 (1986)] found in the Xenopus TFIIIA gene (between fingers 1, 2, and 3), in the Drosophila Kruppel gap gene [Rosenberg et al., Nature, 319, 336-339 (1986)], and in genes from mouse and Xenopus that cross-hybridize to the Kruppel (Kr) finger domains: mkr1, mkr2 [Chowdhury et al., Cell, 48, 771-778 (1987)], and Xfin [Altaba et al., EMBO Journal, 6, 3065-3070 (1987)]. The sequence similarity amongst the Egr-1 fingers is 50-70%, whereas the sequence similarity between any of the Egr-1 fingers and those present in TFIIIA, Kruppel, mkr1, mkr2 or Xfin is 35-40%. Outside of the finger domains, it is noteworthy that the Egr-1 and Kr proteins each contain a very high proportion of Pro, Ala, and Ser residues [Schuh et al., Cell, 47, 1025-1032 (1986)]. However, there is no sequence similarity in these regions. Thus, Egr-1 and Kr are not homologous genes nor is Egr-1 related to mkr1, mkr2, Xfin, or TFIIIA. The Kr gene contains thirteen copies of the hexanucleotide (ACAAAA), or its complementary sequence, eight of which are located within 180 bp downstream from the Kr TATA box and five are in the 3' UT region. These sequences may serve as targets for other DNA binding proteins or in Kr gene autoregulation. The Egr-1 cDNA also contains nine copies of the ACAAAA sequence or its complement.

Following the work described above, Milbrandt [Science, 238, 797-799 (1987)], reported the isolation and sequence of a nerve growth factor (NGF) inducible cDNA (NGFI-A) from the rat pheochromocytom PC12 line. A comparison of the deduced amino acid sequence of NGFI-A to that of mouse Egr-1 of FIGS. 1.1-1.8 reveals 98% sequence identity. Thus, mouse Egr-1 and rat NGFI-A are homologs. The putative initiation ATG chosen by Milbrandt corresponds to position 343 in the FIGS. 1.1-1.8 cDNA sequence, and is 84 nucleotides (28 amino acid residues) downstream of the ATG therein designated for translation initiation. Both ATG's have a purine at position −3 and a'G at position +1 and the designation represented in FIGS. 1.1-1.8 of the more 5' ATG as the putative start codon is based on the experience of Kozak, Nuc. Acids Res., 15, 8125-8131 (1987), even though the more 3' ATG is surrounded by the longer KoLak consensus sequence (CCG/ACCATGG). Translation of an in vitro generated RNA transcript, described infra, selects the more 5' ATG for initiation.

It is noteworthy that a major difference in the deduced sequences of mouse Egr-1 and rat NGFI-A resides in the sequence spanning residues 61-68 of Egr-1 and 33-43 of NGFI-A. The former includes the sequence N-S-S-S-S-T-S-S while the latter includes the sequence N-N-S-S-S-S-S-S-S-S-S, accounting for the 3 residue difference in length of the putative polypeptides which is not accounted for by the difference in designation of the transcript initiation signal.

EXAMPLE 2

Human Chromosome Gene Mapping

To determine the human chromosomal localization of the gene corresponding to mouse Egr-1, the OC3.1 and OC19t cDNA clones were hybridized to a panel of rodent x human somatic cell hybrids. Southern blot analysis of the hybrid panel showed concordance between the presence of Egr-1 sequences and human chromosome 5. In situ hybridization to normal human metaphase chromosomes resulted in specific labeling only of chromosome 5, with the largest cluster of grains at 5q23-31. Specific labeling of these bands was also observed in hybridizations using an Egr-1 probe which does not contain finger sequences.

This localization is interesting in light of the non-random deletions [del(5q)] in human myeloid disorders (acute myelogenous leukemia) (AML), and myelodysplastic syndromes, that involve this chromosomal region. [Le Beau et al., Science, 231, 984-987 (1986); Dewald et al., Blood, 66, 189-197 (1985); and Van den Berghe et al., Cancer Genet. Cytogenet., 17, 189-255 (1985)]. Fifty percent of patients with therapy related AML show chromosome 5 abnormalities (interstitial deletions or monosomy) and cytogenetic analysis of the deletions has revealed that one segment, consisting of bands 5q23-31, is absent in the malignant cells of all patients who have aberrations of chromosome 5. These data suggest that loss of a critical DNA sequence leading to hemizygosity (or homozygosity) of a recessive allele may play an important role in the pathogenesis of these disorders, a mechanism substantiated for retinoblastoma. Although genes for a number of growth factors and receptors (IL-3, GM-CSF, $\beta_2$-adrenergic receptor, endothelial cell growth factor, CSF-1, c-fms, pDGF receptor) are clustered in or near this region, Egr-1 (by virtue of its zinc fingers) is the only member of this group with potential transcriptional regulatory activity. It is therefore possible that its absence could lead to deregulated cell growth.

EXAMPLE 3

In Vitro Expression of Mouse Egr-1 cDNA

A 2.1 kb ApaI/ApaI fragment (comprising nucleotides 120-2224 of FIGS. 1.1-1.8 was isolated from the OC3.1 DNA clone. This fragment includes the translation start (ATG) codon at nucleotide position 259 designated in FIGS. 1.1-1.8. The fragment was blunt-ended with T4 DNA polymerase and cloned into the Bluescript vector KS M13(+) containing a T3/T7 bacteriophage promoter. The (T3) sense transcript was generated and in vitro translated in a standard rabbit reticulocyte lysate system (Promega Biotec, Madison, Wis. 53711) including $^{35}S$ methionine as a radiolabel. An analogous in vitro transcription system was developed using a BglII/BglII fragment of OC3.1 (including nucleotides 301-1958 and not including the translation start designated in FIGS. 1.1-1.8). The T7 sense transcript was employed in the translation system. Differential characterization of translation products by autoradiographic SDS PAGE indicated that the ATG at nucleotide position 259 is preferred as a translation start codon when all potential start sites are present.

EXAMPLE 4

Preparation of Antibodies

A first synthetic peptide based on the sequence of amino acid residues 416–427 of mouse Egr-1 was prepared and provided with a carboxy terminal cysteine residue. The peptide, H-L-R-Q-K-D-K-K-A-D-K-S-C, was coupled to KLH and employed to immunize New Zealand white rabbits. Animals were initially immunized with 100 µg of the immunogen in Freund's Complete Adjuvant and every two weeks were boosted with 100 µg of immunogen with Freund's Incomplete Adjuvant. Sera, designated VPS10, were isolated after 68 days and displayed an antibody titer of 1:12,800 based on reactivity with the antigen used to prepare the antisera.

A second synthetic peptide, based on residues 399 to 415 of mouse Egr-1, was prepared. The peptide, C-G-R-K-R-A-R-S-D-E-R-K-R-H-T-K-I, was coupled to KLH and used to immunize rabbits as above, resulting in the production of antisera (designated VPS2) with a titer of 1:400.

EXAMPLE 5

Isolation of Genomic Mouse Egr-1 Clone and Characterization of Regulatory Regions A 2.4 kb Pvu-II-PvuII fragment and a 6.6 kb XbaI-XbaI fragment (see FIG. 5) derived from the mgEgr-1.1 clone were subcloned into the SmaI and XbaI sites of pUC13 and pUC18 respectively, and the resulting plasmids (designated as p2.4 and p6.6) were used for restriction mapping analysis of transcription initiatin sites and for nucleotide sequencing. Marked in FIGS. 4.1–4.2, and listed in Table 1, are possible regulatory elements identified in the 5' flanking sequence of mgEgr-1.1. A putative TATA motif (AAATA) is located 26 nucleotides upstream of the transcription start site. A "CCAAT" type sequence starts at nucleotide −337. Five different regions, each 10 nucleotides in length, located at −110, −342, −358, −374, and −412, are nearly identical to the inner core of the c-fos serum response element (Treisman, R., Cell, 46, 567 (1986)). Each has a 5–6 nucleotide AT rich stretch and is surrounded by the dinucleotide CC on the 5' side and GG on the other. Two potential TPA responsive elements (Lee, W., et al., Cell, 49, 741 (1987) and Angel, P., et al., Cell, 49, 729 (1987)) are located at nucleotides −610 and −867. Four consensus Sp1 (Briggs, M. R., et al., Science 234, 47 (1986) binding sequences are at position −285, −649, −700 and −719. In addition, two sequences have been identified that might serve as cAMP response elements (Montimy, M. R., et al., Nature, 328, 175 (1987)) (−138 and −631).

TABLE 1

| Location and Identification of Potential Regulatory Elements | | |
|---|---|---|
| Element | Sequence[1] | Location[2] |
| TATA | AAATA | −26 to −22 |
| CCAAT | CCAAT | −337 to −333 |
| Serum Response Element | | |
| Consensus | | |
| GATGTCCATATTAGGACATC | TCCTTCCATATTAGGTTTC | −110 to −91 |
|    CC   TA  AT   GG | GTGGCCC—AATATGGCCCTG | −342 to −324 |
|     G              C | CAGCGCCT TATATGGAGTGG | −358 to −339 |
| | ACAGACCT TATTTGGGCAGC | −374 to −355 |
| | AAACGCCA TATAAGGAGCAG | −412 to −393 |
| TPA Responsive Element | | |
| (AP1 binding site) | | |
| Consensus | | |
| C      C | CTGACTCG | −610 to −603 |
|  TGACT  A | CTGACTGG | −876 to −860 |
| G      A | | |
| Sp1 binding site | GGGCGG | −285 to −280 |
| | GGGCGG | −649 to −644 |
| | CCGCCC | −700 to −695 |
| | GGGCGG | −719 to −714 |
| cAMP Response Element | | |
| Consensus | | |
| TGACGTCA | TCACGTCA | −138 to −131 |
| | TGACGGCT | −631 to −624 |

[1]The underlined bases in the mouse Egr-1 gene sequence are those that do not match the consensus sequence.
[2]The location numbers refer to the nucleotides of the mouse Egr-1 gene as indicated in FIGS. 4.1–4.2

A mouse Balb/c 3T3 genomic library was prepared in a Stratagene (La Jolla, Calif.) vector, λFIX, according to the manufacturer's instructions and probed using 1% SDS, 1 M NaCl, and 10% dextran sulfate at 65° C. with stringent final wash in 0.2×SSC at 65° C. with a 2.1 kb ApaI/ApaI fragment and a 3.1 kb Eco RI/Eco RI fragment derived from digestion of pUC13 including the mouse Egr-1 clone OC3.1. One positive clone, from approximately 300,000 screened, was designated mgEgr-1.1 and also hybridized to the extreme 5'-end 120 bp Eco RI-Apa I fragment from plasmid OC3.1.

Figure 5:
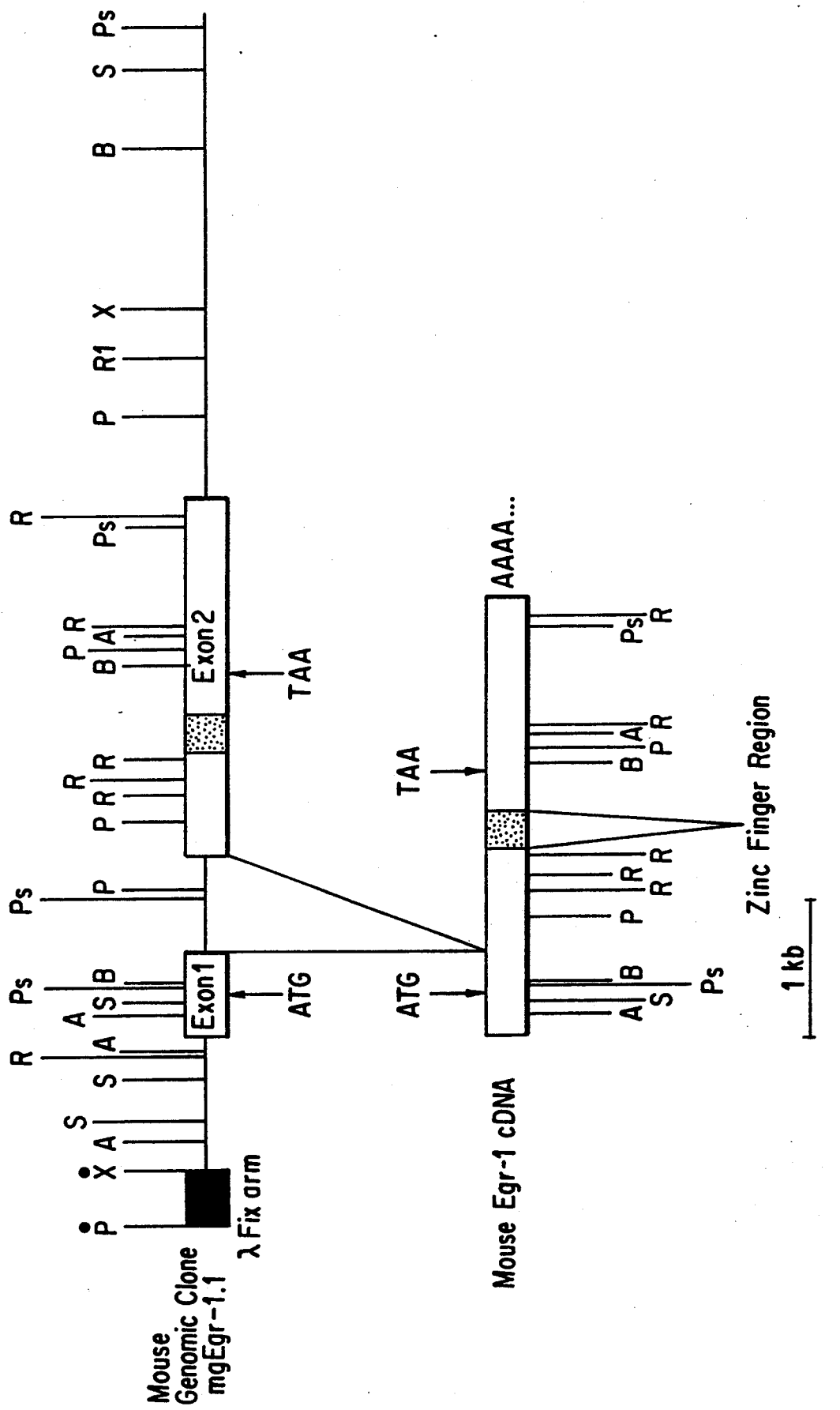

To obtain the genomic sequence and the intronexon gene structure, specific oligonucleotides (17-mers at positions 83, 122, 174, 200, 379, 543, 611, 659, 905, 920, 1000, 1200, 1400, 1600, 1800, 2100, 2353, 2650, 2825) of the OC3.1 cDNA sequence (see FIGS. 1.1–1.8) were used as primers for double stranded sequencing of plasmids p2.4 and p6.6. Comparison of the Egr-1 genomic sequence to the Egr-1 cDNA sequence showed the Egr-1 gene consists of 2 exons and a single 700 bp intron (between nucleotide position 556 and 557 as numbered in FIG. 1A and as shown in FIG. 5). Both the 5' and 3' splice junction sequences (not shown) are in excellent agreement with the consensus boundary sequences. Mount, S. M., *Nucleic Acids Res.*, 10, 459 (1982).

EXAMPLE 6

Isolation and Characterization of Human EGR2 cDNA

A human genomic placental library in the vector EMBL3, prepared by Dr. C. Westbrook of the University of Chicago according to procedures described in Frischauff et al., *Jour. Mol. Biol.*, 170, 827–842 (1983), and a human leukocyte cosmid library prepared according to procedures described in *Proc. Nat'l. Acad. Sci. (USA)*, 80, 5225–5229 (1983), were probed with the 2.1 kb ApaI fragment of OC3.1 (described in Example 5) using 1% SDS, 1 M NaCl and 10% dextrane sulfate at 50°–55° C. with a non-stringent final wash in 2×SSC at 50°–55° C. A single positive clone (designated HG6) was isolated from the first library and four clones (designated HG17, 18, 19 and 21, respectively) were isolated from the second library. A 6.6 kb SalI/EcoRI fragment of clone HG6 was found to hybridize with a 332 base pair HpaII/HpaII fragment of the mouse Egr-1 gene, which letter fragment spans the putative zinc finger region. The 6.6 kb fragment, in turn, was employed to probe a cDNA library derived from human fibroblasts which have been stimulated for three hours with 20% fetal calf serum in the presence of 10 μg/ml cyclohexamide. About 10,000 clones were screened and the fifty positive clones obtained (designated "zap-1 through zap-50") are being subjected to nucleotide sequence analysis. Preliminary sequence analysis reveals that three clones, zap-2, zap-8, and zap-32, all encode the same transcript, namely a protein designated human EGR2, shown in FIGS. 3.1–3.8. Preliminary analysis indicates approximately 92% homology between mouse Egr-1 and human EGR2 polypeptides in the zinc finger regions, but substantially less homology in the amino and carboxy terminal regions. Chromosome mapping studies, similar to those described in Example 2, indicate that human chromosome 10, at bands q21-22, constitutes a locus for the human EGR2 gene.

The plasmid zap-32, containing the full length human EGR2 clone, was used as a probe in Southern blot analysis on DNAs from 58 unrelated Caucasians. It was found that Hind III detects a simple two-allele polymorphism with bands at either 8.0 kb (A1) or 5.6 kb and 2.4 kb (A2). No constant bands were detected. The frequency of A1 was 0.90 and that of A2 was 0.10. No polymorphisms were detected for Apa I, BamH I, Ban II, Bgl I, Bgl II, BstE II, Dra I, EcoR I, EcoR V, Hinc II, Msp I, Pst I, Pvu II, Rsa I, Sac I, and Taq I in 10 unrelated individuals. Co-dominant segregation of the Hind III RFLP was observed in four large kindreds with a total of more than 350 individuals.

These data will be useful in gene linkage studies for mapping genes for certain genetic disorders. For example, the gene responsible for the dominantly inherited syndrome, multiple endocrine neoplasia, type 2A (MEN-2A) has been assigned by linkage to chromosome 10. Simpson, et al., *Nature*, 328, 528 (1987). Studies are currently underway to determine the linkage relationship between MEN-2A and EGR2 and are expected to be useful in cloning the MEN-2A gene as well as in serving as a diagnostic marker for the disease.

EXAMPLE 7

Recombinant Expression Of Fusion Proteins

A 322 base HpaII/HpaII fragment (comprising nucleotides 231–1553) derived from the OC3.1 cloned DNA was treated with DNA polymerase to fill in the single stranded ends. This fragment was inserted in plasmid pEX3 (obtained from K. Stanley, European Molecular Biology Laboratory, Postfach 10.2209, 6900 Heidelberg, (F. R. G.) digested with SmaI. Stanley, K. K., et al., *EMBO J.*, 3, 1429 (1984). This insertion placed the Egr-1 encoding DNA fragment in the same reading frame as plasmid DNA encoding cro-β-galactosidase, allowing for the expression of a fusion protein comprising the amino terminal residues of cro-β-galactosidase and 108 residues of Egr-1 amino acids 325 to 432. This cro-β-galactosidase/Egr-1 fusion plasmid, designated pFIG, was used to transform *E. coli* NF1.

Induced (42° C.) and un-induced (30° C.) cultured cell lysates from growth of the transformed NF1 cells were then analyzed by SDS-PAGE. Upon Coomassie stain analysis, only induced cell lysates included an approximately 108 kd product, indicating presence of the projected expression product. Western blot analysis, using the rabbit polyclonal anti-peptide antibody VPS10 (see Example 4) raised against H-L-R-Q-K-D-K-K-A-D-K-S-C, confirmed that the fusion protein product contained Egr sequences.

In a separate construction, a mouse Egr-1 insert, from plasmid OC3.1, was fused, in frame, to a plasmid containing sequences from bovine growth hormone according to the methods described in Slamon, D. J., et al., *Science*, 233, 347 (1986). The resultant plasmid, designated pV4, comprised a fusion protein containing a fusion gene coding for bovine growth hormone amino acids 1 to 192 and Egr-1 amino acids 2 to 533. This bGH/mouse Egr-1 DNA fusion plasmid, designated pV4, was expressed in *E. coli* and the resulting fusion protein, designated V4, was identified in Western blots by its reactivity with a bGH monoclonal antibody and its reactivity with VPS10 rabbit anti-Egr-1 peptide antiserum, prepared according to Example 4.

EXAMPLE 8

Determination of Egr Levels in Human Tumor and Non-Tumor Tissue

Using the mouse Egr-1 OC68 probe, Northern blot analyses were conducted to determine the levels of transcription of Egr protein encoding DNA in tumor versus surrounding normal tissue from resected human tumor specimens. The tumor samples were from lung (12), colon (7), colon mesastasis (1), bladder (1), rectal (1), giant cell (1), hepatoma (1), breast (1), MFH (malignant fibrous histiocytoma) (1), osteosarcoma (1) and rhabdomyosarcoma (1). In about 50% of these cases, there is markedly decreased (about three to ten-fold) expression of the Egr mRNA in tumor versus normal tissue. One implication of this finding is that Egr proteins of the invention may function as part of a negative regulatory pathway. In any event, it is clear that DNA sequences and antibodies of the invention are susceptible to use in differential diagnoses between tumorous and non-tumorous cell types.

It will be apparent from consideration of the foregoing illustrative examples that the present invention constitutes a substantial advance in the art and the achievement of a major goal in molecular biology, i.e., the characterization of genes which play a regulatory role in mammalian cell proliferation and differentiation. It will thus be understood that the information provided herein constitutes a basis for straightforward development of useful methods and materials not specifically the subject of the above examples. By way of illustration, possession of knowledge concerning the base sequence of cDNA and genomic DNA sequences encoding distinct mouse Egr-1 and human EGR2 early growth regulatory proteins comprising histidine-cysteine zinc finger amino acid sequences makes possible the isolation of other such structurally related proteins. The substantial homology between the zinc finger regions of Egr-1 and EGR2 coupled with lack of homology in other protein regions, when considered in light of the ability of Egr-1 probes to localize to human chromosome 5 while EGR2 probes localize to human chromosome 10, essentially assures the straightforward isolation of a human gene (provisionally designated "human EGR1") which encodes a protein more closely homologous to Egr-1 and a mouse gene (Egr-2) encoding a protein more closely homologous to EGR2.

While the above examples provide only limited illustration of in vitro and in vivo expression of DNA sequences of the invention, known recombinant techniques are readily applicable to development of a variety of procaryotic and eucaryotic expression systems for the large scale production of Egr proteins and even development of gene therapy regimens.

Knowledge of the specifically illustrated mouse Egr-1 and human EGR2 proteins of the invention has been demonstrated to provide a basis for preparation of highly useful antibodies, also provides a wealth of information concerning the nature of protein-nucleic acid interactions which, in turn, constitutes a basis for determination of significant early growth regulatory events. For example, and by analogy to steroid receptor protein structures, analysis of the structure of regions flanking the zinc fingers of Egr-1 and EGR2 and related proteins of the invention is expected to allow for identification of substances which may interact with the proteins to alter their DNA interactive capacities and thus provide the basis for inhibition or augmentation of their regulatory functions. Moreover, information available concerning specific events of DNA interaction of Egr proteins of the invention will permit, e.g., identification and use of potential competitive inhibitors of these proteins.

Just as Egr encoding DNA of the invention is conspicuously susceptible to use in differentiation of human tumor and non-tumor cells, antibodies prepared according to the invention are expected to be useful in differential screening of cells based on relative cellular concentrations of mRNA expression products and in the determination of specific genes susceptible to regulation by such products.

Because numerous modifications and variations in the practice of the present invention are expected to occur to those skilled in the art, only such limitations as appear in the appended claims should be placed thereon.

What is claimed is:

1. A purified and isolated DNA sequence encoding a mammalian early regulatory growth protein which comprises one or more histidine-cysteine finger amino acid sequences, said DNA capable of hybridizing with the mouse Egr-1 gene of FIGS. 1.1-1.8, under hybridization conditions which include 1 M NaCl and 10% dextran sulfate at 50°-65°.

2. The DNA sequence according to claim 1 encoding human EGR2 protein.

3. The DNA sequence according to claim 1 encoding mouse Egr-1 protein.

4. The DNA sequence according to claim 1 which is a cDNA sequence.

5. The DNA sequence according to claim 1 which is a genomic DNA sequence.

6. The DNA sequence according to claim 1 selected from the group sonsisting of the DNA sequences set forth in FIGS. 1.1-1.8, 3.1-3.8 and 4.1-4.2.

7. The DNA sequence according to claim 1 selected from the group consisting of the DNA sequences set forth in FIGS. 1A, 3, and 4.

8. A viral or circular DNA plasmid vector comprising a DNA sequence according to claim 1.

9. The viral or circular DNA plasmid vector according to claim 8 further comprising an expression regulatory sequence operatively associated with said early growth regulatory protein encoding DNA.

10. A procaryotic or eucaryotic host cell transformed or transfected with a vector according to claim 8 or 9.

11. A method for the production of an early growth regulatory protein comprising:
   growing a host cell transformed or transfected with a vector according to claim 10; and
   isolating from said host cell or culture the polypeptide product of the expression of said DNA sequence.

12. A method for the production of an early growth regulatory protein comprising:
   incubating a DNA sequence according to claim 1 in a cell free transcription and translating system; and
   isolating from said system the polypeptide product of the expression of said DNA sequence.

* * * * *

UNITED STATES PATENT AND TRADEMARK OFFICE
CERTIFICATE OF CORRECTION

PATENT NO. : 5,206,152
DATED : April 27, 1993
INVENTOR(S) : Vikas P. Sukhatme

It is certified that error appears in the above-indentified patent and that said Letters Patent is hereby corrected as shown below:

In Column 14 (Claim 6), line 25, change "sonsisting" to --consisting--.

In Column 14 (Claim 11), line 42, change "host cell or culture the" to --host cell the--.

Signed and Sealed this

Twelfth Day of April, 1994

BRUCE LEHMAN

*Commissioner of Patents and Trademarks*

*Attest:*

*Attesting Officer*